United States Patent
Linder et al.

(10) Patent No.: US 6,383,510 B1
(45) Date of Patent: May 7, 2002

(54) SUPPOSITORY FORM COMPRISING AN ACID-LABILE ACTIVE COMPOUND

(75) Inventors: Rudolf Linder; Rango Dietrich, both of Konstanz (DE)

(73) Assignee: Byk Gulden Lomberg Chemische Fabrik GmbH, Konstanz (DE)

( * ) Notice: Subject to any disclaimer, the term of this patent is extended or adjusted under 35 U.S.C. 154(b) by 0 days.

(21) Appl. No.: 09/554,079

(22) PCT Filed: Dec. 8, 1998

(86) PCT No.: PCT/EP98/07946

§ 371 Date: Jul. 6, 2000

§ 102(e) Date: Jul. 6, 2000

(87) PCT Pub. No.: WO99/29299

PCT Pub. Date: Jun. 17, 1999

(30) Foreign Application Priority Data

Dec. 8, 1997 (DE) .......................... 197 54 324
May 20, 1998 (DE) .......................... 198 22 549

(51) Int. Cl.[7] .............. A61F 13/00; A61F 9/02
(52) U.S. Cl. .................... 424/436; 424/434
(58) Field of Search .................. 424/434, 436; 514/338

(56) References Cited

U.S. PATENT DOCUMENTS 5,219,870 A * 6/1993 Kim ................ 514/338
5,635,520 A * 6/1997 Uda ................ 514/338

FOREIGN PATENT DOCUMENTS

| EP | 0 005 129 | 10/1979 |
| EP | 0 277 741 | 8/1988 |
| EP | 0 645 140 | 3/1995 |
| WO | 97/17064 | 5/1997 |
| WO | 98/52564 | 11/1998 |
| WO | 99/32091 | 7/1999 |
| WO | 00/24382 | 5/2000 |

OTHER PUBLICATIONS

Eun et al. Rectal Absorption of Omeprazole from Suppositories in Rabbits. Arch. Pharm. Res. (1995), 18 (4), 219–23.*
Choi et al. Bioavailabilities of Omeprazole Administered to Rats through Various Routes. Arch. Pharm. Res. (1995), 18 (3), 141–5.*
Choi et al. Rectal Absorption of Omeprazole from Suppository in Humans. J. Pharm. Sci. (1996), 85(8) 893–894.*

* cited by examiner

Primary Examiner—Gollamudi S. Kishore
Assistant Examiner—Rachel M. Bennett
(74) Attorney, Agent, or Firm—Jacobson Holman, PLLC

(57) ABSTRACT

Acid-labile active compounds are prepared in suppository form, particularly for rectal administration.

29 Claims, No Drawings

SUPPOSITORY FORM COMPRISING AN ACID-LABILE ACTIVE COMPOUND

This application is a 371 of PCT/EP98/07946 filed Dec. 8, 1998.

TECHNICAL FIELD

The present invention relates to the field of pharmaceutical technology and describes a novel administration form comprising an acid-labile active compound. In particular an acid-labile proton pump inhibitor. The novel administration form is a suppository, in particular for rectal administration. Furthermore, the invention also relates to a process for the production of the administration form and preparations which can be used for the production of the administration form.

Prior Art

Acid-labile proton pump inhibitors ($H^+/K^+$ ATPase inhibitors), In particular pyridin-2-ylmethylsulfinyl-1H-banzimidazoles, such as are disclosed, for example, In EP-A-0 005 129, EP-A-0 166 287, EP-A-0 174 726 and EP-A-0 268 956, are of great importance on account of their $H^+/K^+$ ATPase-inhibiting action in the therapy of diseases which result from increased gastric acid secretion. Examples of already commercially available active compounds from this group are 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole). 2-[3-methyl-4-(2,2,2-trifluoroethoxy)-2-pyridinyl)methylsulfinyl]-1H-benzimidazole (INN: lansoprazole) and 2-{[4-(3-methoxypropoxy)-3-methylpyridin-2yl]methylsulfinyl}-1H-benzimidazole (INN: rabeprazole).

Because of their strong tendency to decompose in a neutral and, in particular, acidic environment, strongly colored decomposition products being formed, it is necessary to protect the active compounds in pharmaceutical administration forms from the action of acids and moisture and destruction by undesired interaction with pharmaceutical auxiliaries. For example, the strongly acid-labile pyridin-2-ylmethylsulfinyl-1H-banzimidazoles for oral administration forms are processed in the tablet core or in pellets in the form of their alkaline salts, for example as sodium salts, or together with alkaline substances.

The preparation of administration forms for acid-labile proton pump inhibitors for oral administration is described, for example, in EP-A-0 244 380, EP-A-0 519 385, EP-A-0 342 522, EP-A-0 277 741, WO 96/01623, WO 98/01624, WO 98/01626 and WO 97/25030.

In certain groups of patients the oral administration of an active compound is not possible or is made difficult, for example in the case of patients having a hypersensitivity to taste impulses, in the case of difficulty in swallowing, after stomach operations or in patients in intensive care units. In these cases, the administration of an active compound can be affected by means of a suppository.

EP-0 645 140 describes compositions for rectal administration in which pyridin-2-ylmethylsulfinyl-1H-benzimidazoles and salts of fatty acids having 6–20 C atoms are present mixed in a base for rectal administration.

In WO 97/34580, a suppository for acid-labile active compounds is described which, in addition to the active compound, contains poloxamer and hydrophilic natural polymers as auxiliaries.

EP-0 444 625 discloses omeprazole compositions for rectal administration, which contain omeprazole as an active compound, a mixture of polyethylene glycols or a mixture or hard fat and sodium lauryl sulfate as well as a soluble basic amino acid.

DESCRIPTION OF THE INVENTION

It is an object of the present invention to provide a novel, stable suppository form for add-labile active compounds.

It has now surprisingly been found that this object can be achieved by a suppository which comprises a plurality of individual active compound units, the acid-labile active compound in the individual active compound units being surrounded by a mixture or at least one sterol and at least one polymer, by at least one fatty alcohol or by a mixture of at least one fatty alcohol and at least one polymer and/or at least one sterol.

The subject of the invention is a suppository for acid-labile active compounds, comprising at least one pharmaceutical auxiliary and a plurality of individual active compound units, wherein the acid-labile active compound in the individual active compound units is surrounded by a mixture of at least one sterol and at least one polymer, by at least one fatty alcohol or by a mixture of at least one fatty alcohol and at least one polymer and/or at least one sterol.

A preferred subject of the invention is a suppository for acid-labile active compounds, comprising at least one pharmaceutical auxiliary and a plurality of individual active compound units, wherein the acid-labile active compound in the individual active compound units is surrounded by a mixture of at least one sterol and at least one polymer.

Further subjects follow from the patent claims.

The plurality of individual active compound units in the sense of the invention is a plurality of individual units (multiple individual units) in which at least one active compound particle is present surrounded by a mixture of at least one sterol and at least one polymer, by at least one fatty alcohol or by a mixture of at least one fatly alcohol and at least one polymer and/or at least one sterol.

Further subject of the invention is an active compound unit comprising an acid-labile active compound, wherein the acid-labile active compound is surrounded by a mixture of at least one sterol and at least one polymer, by at least one fatty alcohol or by a mixture of at least one fatty alcohol and at least one polymer and/or at least one sterol.

The particle size of the individual units is advantageously less than 200 µm. In particular less than 100 µm. Preferably, the particle size is in the range from 2 µm to 50 µm, particularly preferably in the range from 4 µm to 20 µm.

Acid-labile active compounds in the sense of the present invention are, in particular, acid-labile proton pump inhibitors.

Acid-labile proton pump inhibitors ($H^+/K^+$ ATPase inhibitors) which may be mentioned in the sense of the present invention are, in particular, substituted pyridin-2-ylmethylsulfinyl-1H-benzimidazoles, such as are disclosed, for example, in EP-A-0 005 129, EP-A-0 165 287, EP-A-0 174 726, EP-A-0 184 322, EP-A-0 261 478 and EP-A-0 258 956. Preferably, mention may be made here of 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-2,2,2-trifluoroethoxy)-2-pyridinyl)methylsulfinyl]-1H-benzimidazole (INN: lansoprazole) and 2-{[4(3- methoxypropoxy)-3-methylpyridin-2-yl]methylsulfinyl}-1H-benzimidazole (INN: rabeprazole).

Further acid-labile proton pump inhibitors, for example substituted phenylmethylsulfinyl-1H-benzimidazoles, cycloheptapyridin-9-ylsulfinyl-1H-benzimidazoles or pyridin-2-ylmethylsulfinylthienoimidazoles are disclosed in DE-A-35 31 487, EP-A-0 434 999 or EP-A-0 234 485. Mention may be made by way of example of 2-[2-(N-isobutyl-N-methylamino)benzylsulfinyl]benzimidazole (INN: leminoprazole) and 2-(4-methoxy-6,7,8,9-tetrahydro-5H-clohepta[b]pyridin-9-ylsulfinyl)-1H-benzimidazole (INN: nepaprazole).

The acid-labile proton pump inhibitors are chiral compounds. The term acid-labile proton pump inhibitor also includes the pure enantiomers of the acid-labile proton pump inhibitors and their mixtures in any mixing ratio including the racemates. Enantiomerically pure acid-labile proton pump inhibitors are disclosed, for example, in WO 92/08716. Esomeprazole may be mentioned by way of example.

The acid-labile proton pump inhibitors are present here as such or preferably in the form of their salts with bases. Examples of salts with bases which may be mentioned are sodium, potassium, magnesium or calcium salts. If desired, the salts of the acid-labile proton pump inhibitors with bases can also be present in hydrate form. Such a hydrate of the salt of an acid-labile proton pump inhibitor with a base is disclosed, for example, in WO 91/19710.

Particularly preferred acid-labile proton pump inhibitors which may be mentioned are pantoprazole sodium and pantoprazole sodium sesquihydrate (=pantoprazole sodium× 1.5 $H_2O$).

The sterol is preferably a phytosterol or a zoosterol. Phytosterols which may be mentioned by way of example are ergosterol, stigmasterol, sitosterol, brassicasterol and campesterol. Zoosterols which may be mentioned by way of example are cholesterol and lanosterol. If desired, mixtures of sterols can also be present.

The polymer is preferably a polymer having nonacidic groups. Polymers which may be mentioned by way of example are polyvidone (e.g. Kollidon 17, 30 and 90 from BASF), vinylpyrrolidone/vinyl acetate copolymer and polyvinyl acetate. Cellulose ethers such as, for example, methylcellulose, ethylcellulose Ethocel) and hydroxypropylmethylcellulose and cellulose esters (e,g, cellulose acetate phthalate) may furthermore be mentioned. If desired, mixtures of polymers can also be present.

The fatty alcohol is preferably a linear, saturated or unsaturated primary alcohol having 10–30 carbon atoms. Fatty alcohols which may be mentioned by way of example are cetyl alcohol, myristyl alcohol or stearyl alcohol. If desired, mixtures of fatty alcohols can also be present.

The amount (in % by weight) of active compound in the individual active compound unit is advantageously 1–90%. In case of units in which at least one active compound particle is present, surrounded by a mixture of at least one sterol and at least one polymer the amounts of sterol and of polymer are in each case advantageously 5–80%. Preferably, the amount of active compound is 10–50%, the amount of sterol is 10–40% and the amount of polymer is 10–50%.

In case of units in which at least one active compound particle is present, surrounded by at least one fatty alcohol, preferably the amount of active compound is 2–70% and the amount of fatty alcohol is 30–98%.

In case of units in which at least one active compound particle is present, surrounded by at least one fatty alcohol and at least one sterol, preferably the amount of active compound is 2–70%, the amount of fatty alcohol is 20–90% and the amount of sterol is 8–50%.

In case of units in which at least one active compound particle is present, surrounded by at least one fatty alcohol and at least one polymer, preferably the amount of active compound is 10–60%, the amount of fatty alcohol is 10–60% and the amount of polymer is 10–40%.

In case of units in which at least one active compound particle is present, surrounded by at least one fatty alcohol, at least one polymer and at least one sterol, preferably the amount of active ingredient is 2–70%, the amount of fatty alcohol is 20–85%, the amount of polymer is 2–25% and the amount of sterol is 10–50%.

It is possible for the person skilled in the arts on account of his/her expert knowledge, to select the best suited sterols, polymers and fatty alcohols depending on the active compound.

The individual active compound units can be prepared, for example, by spray-congealing (spray-solidification) or preferably by spray-drying. Preferably spray-drying is used for the preparation of individual active compound units in which the active compound is surrounded by a mixture of at least one sterol and at least one polymer. Spray-drying takes place from a suitable solvent. Suitable solvents for the spray-drying are preferably those in which the sterol and the polymer are soluble, while the active compound is insoluble. Suitable solvents can also be solvent mixtures.

If an acid-labile proton pump inhibitor, in particular a substituted pyridin-2-ylmethylsulfinyl-1H-benzimidazole, is employed as the active compound, the suitable solvents are, for example, hydrocarbons, chlorinated hydrocarbons and ethyl acetate. Hydrocarbons which may be mentioned are, in particular, linear or branched alkanes or alternatively cycloalkanes. Examples of linear alkanes are pentane, hexane and heptane. Examples of branched alkanes which may be mentioned are 2-methylpantane and 3-mathylpentane. Examples of cycloalkanes which may be mentioned are cyclohexane and cyclopentane. If desired, mixtures of the hydrocarbons such as, for example, petroleum ether can also be employed. As a chlorinated hydrocarbon, chloroform and preferably dichloromethane may be mentioned.

On account of his/her expert knowledge in the field of spray-drying and, if necessary, by means of customary tests, it is possible for the person skilled in the art, depending on the active compound employed, to select the best suited sterols, polymers and solvents.

For spray-drying, the sterol and the polymer are dissolved in the suitable solvent and the active compound is suspended therein. If desired, the active compound can also be suspended first and the sterol and polymer then dissolved. The suspension obtained is then sprayed in a spray-dryer.

Spray-drying is carried out in a manner known per se. A detailed presentation of this technique is found in K Masters, Spray Drying Handbook, 5th edition 1991, and J. Broadhead, S. K. Edmond Ronan, C. T. Rhodes, The Spray Drying of Pharmaceuticals, Drug Dev. Ind, Pharm. 18, 1169 (1992). The principle of spraying consists in breaking down a solution or suspension of the product to be dried into fine droplets and drying it using a hot stream of gas. The solid component remaining after evaporation of the solvent is separated off from the stream of gas by means of a cyclone and/or by a filter unit and collected.

Possible drying gases are, in particular, air and preferably nitrogen. The gas inlet temperature depends on the solvent.

Further subject of the invention is a preparation comprising an acid-labile active compound, at least one sterol and at least one polymer obtainable by spray-drying of a suspension of the acid-labile active compound in a solution of the sterol and the polymer in a suitable solvent Preferably spray-congealing is used for the preparation of individual active compound units in which the active compound is surrounded by at least one fatty alcohol or by a mixture of at least one fatty alcohol and at least one polymer and/or at least one sterol.

For spray-congealing the fatty alcohol is fused and, if desired, the polymer and/or the sterol are dissolved therein to give a homogeneous solution. The active compound is then suspended in the solution. The suspension obtained is then sprayed in a spray-dryer.

Spray-congealing is carried out in a manner known per se. A detailed presentation of this technique is found for example in P. B. Deasy, Microencapsulation and Related Drug Process (1984).

Further subject of the invention is a preparation comprising an acid-labile active compound, at least one fatty alcohol or a mixture of at least one fatty alcohol and at least one polymer and/or sterol obtainable by spray-congealing of a suspension of the acid-labile compound in a solution, if desired, of the polymer and/or sterol in the fatty alcohol.

The particle size of the active compound used in the spray-drying or spray-congealing process is advantageously less than 100 μm preferably less than 40 μm. Preferably, the particle size is in the range from 1–20 μm, particularly preferably in the range from 3–15 μm. Such particle size of the active compound for example can be achieved by mixing the active compound in a suitable mill.

The individual active compound units, subsequently also designated as preparations, can then serve as a base for the production of the suppositories according to the invention.

Preferred suppositories which may be mentioned in this case are those which are suitable for rectal administration. The suppositories according to the invention are in this case prepared in a manner known to the person skilled in the art. For example, a suitable suppository base is fused and a preparation according to the invention is suspended therein. The suspension obtained is then brought into a form customary for suppositories in particular, the suspension is cast to give a suppository shape suitable for rectal administration. Suitable suppository bases which may be mentioned are, for example, the hard fats customarily used or the production of rectal suppositories (subsequently also designated as Adeps solidus or Adeps neutralis). Hard fats are mixtures of mono-, di- and triglycerides which are obtained by esterification of fatty acids (European Pharmacopoeia, 3rd edition 1997, Deutscher Apo-theker Verlag Stuttgart, p. 1022: The United States Pharmacopoeia, USP23, NF18). Such hard fats are commercially available, for example, under the name Witepsol® (e.g. Witepsol® H12 or Witepsol® W31). If desired, further pharmaceutically acceptable auxiliaries, such as, for example, stabilizers. consistency-improving additives or auxiliaries which bring about a uniform distribution of the active compound in the suppository base, can be added.

The suppositories according to the invention contain the acid-labile active compound in a dose customary for the treatment of the appropriate disorder. The suppositories according to the invention comprising acid-labile proton pump inhibitors are suitable for the treatment and prevention of all diseases for the treatment or prevention of which pyridin-2ylmethylsulfinyl-1H-benzmidazoles are employed. In particular the suppositories according to the invention can be employed in the treatment of diseases of the stomach.

Thus, the suppositories according to the invention contain between 1 and 500 mg, preferably between 5 and 60 mg, of an acid-labile proton pump inhibitor. Examples which may be mentioned are suppositories which contain 10, 20, 40 or 50 mg of pantoprazole sodium sesquihydrate. The daily dose (e.g. 40 mg of active compound) can in this case be administered in the form of a single administration or in several administrations using the suppositories according to the invention.

The suppositories comprising acid labile compounds according to the invention can also be combined with other active compounds, either in fixed or in free combination. Fixed combination in this connection relates to an administration form wherein all active compounds are present in a single dosage unit. Free combination in this connection relates to an administration form, wherein the active compounds are present in separated dosage units, in connection with suppositories comprising acid-labile proton pump inhibitors a combination with antimicrobially active compounds or NSAIDs (non steroidal anti inflammatory drugs) may be mentioned. Particularly mention may be made of a combination with anti-microbially active compounds which can be used in the control of Helicobacter pylori (H. pylori).

Examples of suitable antimicrobially-active ingredients (active against Helicobacter pylori) are enumerated in European Patent Application EP-A-282131. These active ingredients include, for example, bismuth salts (such as bismuth subcitrate or bismuth subsalicylate), sulfonamides, nitrofurans (such as nitrofurazone, nitrofurantoin or furazolidone), metronidazole, tinidazole, nimorazole or antibiotics, Examples of antibiotics which may be mentioned in this connection are, arranged according to particular classes of active ingredient: aminoglycosides, such as gentamicin, neomycin, kanamycin, amikacin or streptomycin; macrolides such as erythromycin, azithromycin, clarithromycin, clindamycin or rifampicin; penicillins, such as penicillin G, penicillin V, ampicillin, meziocillin or amoxicillin; polypeptides, such as bacitracin or polymyxin: tetracyclines, such as tetracycline, chlorotetracycline, oxytetracycline, minocycline or doxycycline; carbapenems, such as imipenem, loracarbef, meropenem or panipenem; cephalosporins, such as cefalexin, cefalexin, cefuraxime axetil, cefotaxime, cefpodoxime proxetil, cefaclor, cefadroxil or cephalothin: gyrase inhibitors, such as ciprofloxacin, norfloxacin, ofloxacin or peflaxacin; or other different antibiotics, such as chloramphenicol. Particularly worthy of mention in this connection is also the combination of a plurality of antimicrobially-active ingredients, for example the combination of a bismuth salt and/or tetracycline with metronidazole, or the combination of amoxicillin or clarithromycin with metronidazole and amoxicillin with clarithromycin.

Particularly worthy of mention in this connection is also administration of a proton pump inhibitor together with a plurality of antimicrobially-active ingredients, for example with the combination of a bismuth salt and/or tetracycline with metronidazole or with the combination of amoxicillin or clarithromycin or with metronidazole.

The preparation of suppositories according to the invention is described by way of example below. The examples below illustrate the invention in greater detail without restricting it.

Production of the Preparations by Spray-drying

EXAMPLE 1

7.0 g of cholesterol and 5.0 g of Ethocel are dissolved in 100 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 51° C., pump output 10%. A white, free-flowing powder is obtained.

EXAMPLE 2

5.0 g of cholesterol and 5.0 g of Kollidon 17 are dissolved in 80 ml of dichloramethane. 5.0 g of omeprazole magnesium are suspended in the solution. The suspension is spray-dried in a laboratory spray-dryer (Büchi Mini Spray Dryer B191). Spray conditions: drying gas nitrogen, inlet temperature 51° C.; pump output 10%. A white, free-flowing powder is obtained.

EXAMPLE 3

5.0 g of cholesterol and 8.0 g of polyvidone 17 PF are dissolved in 60 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 52° C.; pump output 12%. A white, free-flowing powder is obtained.

EXAMPLE 4

5.0 g of cholesterol and 8.0 g of polyvidone 17 PF and 2.0 g of ethylcellulose are dissolved in 60 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 52° C.; pump output 12%. A white, free-flowing powder is obtained.

EXAMPLE 5

5.0 g of β-sitosterol, 8.0 g of polyvidone 17 PF and 1.0 g of ethylcellulose are dissolved in 60 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 52° C.; pump output 12%. A white, free-flowing powder is obtained.

The preparations obtained according to Examples 1 to 5 have a particle size in the range 10–40 μm. By variation of the spraying conditions, it is possible, for example, to obtain larger or smaller particles.

Production of the Preparations by Spray-congealing

EXAMPLE 6

100 g of cetyl alcohol are heated to 65° C. 50 g of pantoprazole sodium sesquihydrate are slowly added. The mixture is stirred until a homogeneous suspension is obtained and subsequently sprayed through a nozzle in a spray dryer.

EXAMPLE 7

80 g of stearyl alcohol and 10 g of ethylcellulose are heated to 70° C. and stirred until a clear solution is obtained. 40 g of pantoprazole sodium sesquihydrate are added and stirred. The homogeneous suspension is spray-congealed in a spray dryer.

Preparation of the Suppositories

EXAMPLE A 194.7 g of suppository base (Adeps solidus/neutralis) are fused to give a clear mass at 40–45° C. After coating the mass to 39–40° C., the preparation obtained in Example 1 (15.3 g) is introduced homogeneously using a stirrer. The suspension obtained is cooled to 37–38° C. and cast into suppositories of 2.1 g each.

EXAMPLE B 193.8 g of suppository base (Adeps solidus/neutralis) are fused to give a clear mass at 40–45° C. After cooling the mass to 39–40° C., the preparation obtained in Example 3 (16.2 g) is introduced homogeneously using a stirrer. The suspension obtained is cooled to 37–38° C. and cast into suppositories of 2.1 g each.

EXAMPLE C 192.0 g of suppository base (Adeps solidus/neutralis) are fused to give a clear mass at 40–45° C. After cooling the mass to 39–40° C., the preparation obtained in Example 4 (18.0 g) is introduced homogeneously using a stirrer. The suspension obtained is cooled to 37–38° C. and cast into suppositories of 2.1 g each.

EXAMPLE D 192.9 g of suppository base (Adeps solidus/neutralis) are fused to give a clear mass at 40–45° C. After cooling the mass to 39–40° C., the preparation obtained in Example 5 (17.1 g) is introduced homogeneously using a stirrer. The suspension obtained is cooled to 37–38° C. and cast into suppositories of 2.1 g each.

The suppositories obtained according to Examples A to D in each case contain 45.6 mg of pantoprazole sodium sesquihydrate.

What is claimed is:

1. A suppository for an acid-labile active compound wherein the acid-labile compound is an acid-labile proton pump inhibitor, a salt of an acid-labile proton pump inhibitor with a base or a hydrate of a salt of an acid-labile proton pump inhibitor with a base comprising at least one pharmaceutical auxiliary and a plurality of individual active compound units, wherein the acid-labile active compound in each individual active compound unit is surrounded by a mixture of at least one sterol and at least one polymer, by at least one fatty alcohol or by a mixture of at least one fatty alcohol and at least one polymer and/or at least one sterol.

2. The suppository as claimed in claim 1, wherein the acid-labile active compound in an individual active compound unit is surrounded by a mixture of at least one sterol and at least one polymer.

3. The suppository as claimed in claim 2, wherein the amount (in % by weight) of acid-labile active compound in the individual active compound unit is from 10 to 50%, the amount of sterol is from 10 to 40% and the amount of polymer is from 10 to 50%.

4. The suppository as claimed in claim 1, wherein the acid-labile active compound in each individual active compound unit is surrounded by at least one fatty alcohol, by a mixture of at least one fatty alcohol and at least one polymer, or by a mixture of at least one fatty alcohol and at least one sterol.

5. The suppository as claimed in claim 4, wherein the acid-labile active compound in each individual active compound units is surrounded by at least one fatty alcohol.

6. The suppository as claimed in claim 5, wherein the amount (in % by weight) of acid-labile active compound in each individual active compound unit is from 2 to 70% and the amount of fatty alcohol is from 30 to 98%.

7. The suppository as claimed in claim 4, wherein the acid-labile active compound in each individual active compound unit is surrounded by a mixture of at least one fatty alcohol and at least one polymer.

8. The suppository as claimed in claim 7, wherein the amount (in % by weight) of acid-labile active compound in each individual active compound unit is from 10 to 60%, the amount of fatty alcohol is from 10 to 50% and the amount of polymer is from 10 to 40%.

9. The suppository as claimed in claim 4, wherein the acid-labile active compound in each individual active compound unit is surrounded by a mixture of at least one fatty alcohol and at least one sterol.

10. The suppository as claimed in claim 9, wherein the amount (in % by weight) of acid-labile active compound in each individual active compound unit is from 2 to 70%, the amount of fatty alcohol is from 20 to 90% and the amount of sterol is from 8 to 50%.

11. The suppository as claimed in claim 1, wherein the acid-labile active compound in each individual active compound unit is surrounded by a mixture of at least one fatty alcohol, at least one polymer and at least one sterol.

12. The suppository as claimed in claim 11, wherein the amount (in % by weight) of acid-labile active compound in each individual active compound unit is from 2 to 70%, the amount of fatty alcohol is from 20 to 85%, the amount of polymer is from 2 to 25% and the amount of sterol is from 10 to 50%.

13. The suppository as claimed in claim 1, wherein the acid-labile proton pump inhibitor is pantoprazole, esomeprazole, omeprazole, lansoprazole or rabeprazole.

14. The suppository as claimed in claim 1, wherein the acid-labile proton pump inhibitor is pantoprazole sodium sesquihydrate.

15. The suppository as claimed in claim 1, wherein the sterol is a member selected from the group consisting of cholesterol, lanosterol, ergosterol, stigmasterol, sitosterol, brassicasterol, campesterol and a mixture thereof.

16. The suppository as claimed in claim 1, wherein the polymer is a member selected from the group consisting of polyvidone, vinylpyrrolidone/vinyl acetate copolymer, polyvinyl acetate, methylcellulose, ethylcellulose, hydroxypropylcellulose, cellulose ester and a mixture thereof.

17. The suppository as claimed in claim 1, wherein the fatty alcohol is a member selected from the group consisting of cetyl alcohol, myristyl alcohol, stearyl alcohol and a mixture thereof.

18. The suppository as claimed in claim 1, wherein the pharmaceutical auxiliary is hard fat.

19. The suppository as claimed in claim 18, wherein the hard fat is a member selected from the group consisting of adeps neutralis and adeps solidus.

20. The suppository as claimed in claim 1, wherein the individual active compound units have a particle size less than 200 $\mu$m.

21. The suppository as claimed in claim 1, wherein the individual active compound units have a particle size less than 100 $\mu$m.

22. The suppository as claimed in claim 1, wherein the individual active compound units have a particle size in the range from 4–20 $\mu$m.

23. A process for the production of a suppository as claimed in claim 1, wherein individual active compound units are introduced into a suitable suppository base and converted into a form suitable for administration of suppositories.

24. A process for the production of a suppository as claimed in claim 2, which comprises dissolving at least one sterol and at least one polymer in a suitable solvent, suspending the acid-labile proton pump inhibitor therein, spray-drying the obtained suspension, introducing the individual active compound units produced into a suitable suppository base, and converting the base into a form suitable for administration of suppositories.

25. A suppository obtainable by a process according to claim 24.

26. A process for the production of a suppository as claimed in claim 4 which comprises a) fusing the fatty alcohol and optionally dissolving the polymer and/or the sterol, b) suspending the acid-labile active compound therein, c) spray-congealing the obtained suspension, d) introducing the individual active compound units produced into a suitable suppository base, and e) converting the base into a form suitable for administration of suppositories.

27. A suppository obtainable by a process according to claim 26.

28. A suppository comprising an acid labile proton pump inhibitor, at least one sterol and at least one polymer obtainable by spray-drying a suspension of the acid-labile proton pump inhibitor in a solution of the sterol and the polymer in a suitable solvent.

29. A suppository comprising an acid-labile proton pump inhibitor and
   a) at least one fatty alcohol obtainable by spray congealing a suspension of the acid-labile compound in the fatty alcohol, or
   b) a mixture of at least one fatty alcohol and at least one polymer obtainable by spray congealing a suspension of the acid-labile compound in a solution of the polymer in the fatty alcohol, or
   c) a mixture of at least one fatty alcohol and at least one sterol obtainable by spray congealing a suspension of the acid-labile compound in a solution of the sterol in the fatty alcohol, or
   d) a mixture of at least one fatty alcohol, at least one polymer and at least one sterol obtainable by spray congealing a suspension of the acid-labile compound in a solution of the polymer and sterol in the fatty alcohol.

* * * * *